(12) United States Patent
Yu et al.

(10) Patent No.: US 8,182,720 B2
(45) Date of Patent: *May 22, 2012

(54) SOLUTION-BASED FABRICATION OF PHOTOVOLTAIC CELL

(75) Inventors: Dong Yu, Fremont, CA (US);
Jacqueline Fidanza, San Francisco, CA (US); Brian M. Sager, Menlo Park, CA (US)

(73) Assignee: Nanosolar, Inc., San Jose, CA (US)

( * ) Notice: Subject to any disclaimer, the term of this patent is extended or adjusted under 35 U.S.C. 154(b) by 1017 days.

This patent is subject to a terminal disclaimer.

(21) Appl. No.: 11/933,136

(22) Filed: Oct. 31, 2007

(65) Prior Publication Data
US 2008/0142081 A1   Jun. 19, 2008

Related U.S. Application Data

(63) Continuation of application No. 10/782,017, filed on Feb. 19, 2004, now Pat. No. 7,663,057.

(51) Int. Cl.
*H01B 1/02* (2006.01)
*H01B 1/22* (2006.01)

(52) U.S. Cl. ............ 252/512; 252/519.3; 252/500; 252/518.1; 252/519.1; 136/262; 136/265; 427/216; 427/217; 427/381; 106/266

(58) Field of Classification Search ........... 252/519.3, 252/500, 512, 518.1, 519.1; 136/262, 265; 427/216, 217, 381; 106/266.2, 266
See application file for complete search history.

(56) References Cited

U.S. PATENT DOCUMENTS

| | | | |
|---|---|---|---|
| 3,423,301 A | 1/1969 | Stearns | |
| 3,586,541 A | 6/1971 | Chamberlin | |
| 3,818,324 A | 6/1974 | Espinasse | |
| 3,903,427 A | 9/1975 | Pack | |
| 3,903,428 A | 9/1975 | Dejong | |
| 3,966,568 A | 6/1976 | Crossley et al. | |
| 4,191,794 A | 3/1980 | Shirland et al. | |
| 4,192,721 A | 3/1980 | Fawcett et al. | |
| 4,404,422 A | 9/1983 | Green et al. | |
| 4,522,663 A | 6/1985 | Ovshinsky et al. | |
| 4,536,607 A | 8/1985 | Wiesmann | |
| 4,622,432 A | 11/1986 | Yamazaki | |
| 4,642,140 A | 2/1987 | Noufi et al. | |
| 4,677,250 A | 6/1987 | Barnett et al. | |
| 4,806,436 A | 2/1989 | Tada et al. | |
| 4,940,604 A | 7/1990 | Suyama et al. | |
| 5,013,464 A | 5/1991 | Sugimura et al. | |
| 5,045,409 A | 9/1991 | Eberspacher et al. | |
| 5,078,804 A | 1/1992 | Chen et al. | |
| 5,141,564 A | 8/1992 | Chen et al. | |
| 5,221,435 A | 6/1993 | Smith, Jr. | |
| 5,244,509 A | 9/1993 | Arao et al. | |
| 5,277,786 A | 1/1994 | Kawakami | |
| 5,286,306 A | 2/1994 | Menezes | |
| 5,356,839 A | 10/1994 | Tuttle et al. | |
| 5,401,573 A | 3/1995 | Babel et al. | |
| 5,419,781 A | 5/1995 | Hamakawa et al. | |
| 5,436,204 A | 7/1995 | Albin et al. | |
| 5,441,897 A | 8/1995 | Noufi et al. | |
| 5,445,847 A | 8/1995 | Wada et al. | |
| 5,538,903 A | 7/1996 | Aromoto et al. | |
| 5,567,469 A | 10/1996 | Wada et al. | |
| 5,578,503 A | 11/1996 | Karg et al. | |
| 5,626,688 A | 5/1997 | Probst et al. | |
| 5,633,033 A | 5/1997 | Nishitani et al. | |
| 5,677,250 A | 10/1997 | Knapp | |
| 5,728,231 A | 3/1998 | Negami et al. | |
| 5,730,852 A | 3/1998 | Bhattacharya et al. | |
| 5,925,228 A | 7/1999 | Panitz et al. | |
| 5,945,217 A | 8/1999 | Hanrahan | |
| 5,985,691 A | 11/1999 | Basol et al. | |
| 5,994,163 A | 11/1999 | Bodegard et al. | |
| 6,022,487 A | 2/2000 | Daume et al. | |
| 6,103,459 A * | 8/2000 | Diel | 430/530 |
| 6,107,562 A | 8/2000 | Hashimoto et al. | |
| 6,121,541 A | 9/2000 | Arya | |
| 6,124,039 A | 9/2000 | Goetz et al. | |

(Continued)

FOREIGN PATENT DOCUMENTS
DE   2741954   3/1979
(Continued)

OTHER PUBLICATIONS

U.S. Appl. No. 11/933,407, filed on Oct. 31, 2007 titled "Solution-based Fabrication of Photovoltaic Cell".

(Continued)

*Primary Examiner* — Douglas MC Ginty

(57) ABSTRACT

An ink for forming CIGS photovoltaic cell active layers is disclosed along with methods for making the ink, methods for making the active layers and a solar cell made with the active layer. The ink contains a mixture of nanoparticles of elements of groups IB, IIIA and (optionally) VIA. The particles are in a desired particle size range of between about 1 nm and about 500 nm in diameter, where a majority of the mass of the particles comprises particles ranging in size from no more than about 40% above or below an average particle size or, if the average particle size is less than about 5 nanometers, from no more than about 2 nanometers above or below the average particle size. The use of such ink avoids the need to expose the material to an $H_2Se$ gas during the construction of a photovoltaic cell and allows more uniform melting during film annealing, more uniform intermixing of nanoparticles, and allows higher quality absorber films to be formed.

18 Claims, 1 Drawing Sheet

U.S. PATENT DOCUMENTS

| | | | |
|---|---|---|---|
| 6,124,041 A | 9/2000 | Aoude et al. | |
| 6,126,740 A * | 10/2000 | Schulz et al. | 117/4 |
| 6,127,202 A | 10/2000 | Kapur et al. | |
| 6,150,022 A | 11/2000 | Coulter et al. | |
| 6,228,904 B1 | 5/2001 | Yadav et al. | |
| 6,268,014 B1 | 7/2001 | Eberspacher et al. | |
| 6,323,417 B1 | 11/2001 | Gillespie et al. | |
| 6,344,272 B1 | 2/2002 | Oldenburg et al. | |
| 6,454,886 B1 | 9/2002 | Martin et al. | |
| 6,472,459 B2 | 10/2002 | Morales et al. | |
| 6,518,086 B2 | 2/2003 | Beck et al. | |
| 6,593,690 B1 | 7/2003 | McCormick et al. | |
| 6,641,898 B2 | 11/2003 | Yazaki et al. | |
| 6,685,986 B2 | 2/2004 | Oldenburg et al. | |
| 6,897,603 B2 | 5/2005 | Mao et al. | |
| 6,946,597 B2 * | 9/2005 | Sager et al. | 136/263 |
| 6,974,976 B2 | 12/2005 | Hollars | |
| 6,992,202 B1 * | 1/2006 | Banger et al. | 556/28 |
| 7,115,304 B2 * | 10/2006 | Roscheisen et al. | 427/248.1 |
| 7,144,627 B2 | 12/2006 | Halas et al. | |
| 7,227,066 B1 | 6/2007 | Roscheisen et al. | |
| 7,253,017 B1 | 8/2007 | Roscheisen et al. | |
| 7,306,823 B2 * | 12/2007 | Sager et al. | 427/217 |
| 7,604,843 B1 | 10/2009 | Robinson et al. | |
| 7,605,328 B2 * | 10/2009 | Sager et al. | 136/265 |
| 7,663,057 B2 * | 2/2010 | Yu et al. | 136/264 |
| 7,700,464 B2 * | 4/2010 | Robinson et al. | 438/502 |
| 8,038,909 B2 | 10/2011 | Yu et al. | |
| 2002/0006470 A1 | 1/2002 | Eberspacher et al. | |
| 2002/0132045 A1 | 9/2002 | Halas et al. | |
| 2002/0160195 A1 | 10/2002 | Halas et al. | |
| 2002/0187347 A1 | 12/2002 | Halas et al. | |
| 2003/0051664 A1 | 3/2003 | Stanbery | |
| 2003/0052382 A1 | 3/2003 | Stanbery | |
| 2003/0052391 A1 | 3/2003 | Stanbery | |
| 2003/0054582 A1 | 3/2003 | Stanbery | |
| 2003/0054661 A1 | 3/2003 | Stanbery | |
| 2003/0054662 A1 | 3/2003 | Stanbery | |
| 2003/0054663 A1 | 3/2003 | Stanbery | |
| 2003/0064292 A1 * | 4/2003 | Neudecker et al. | 429/235 |
| 2003/0102023 A1 * | 6/2003 | Delahoy | 136/262 |
| 2003/0192584 A1 | 10/2003 | Montello et al. | |
| 2003/0205270 A1 | 11/2003 | Stanbery | |
| 2003/0211369 A1 | 11/2003 | Riman et al. | |
| 2003/0211646 A1 | 11/2003 | Stanbery | |
| 2004/0063320 A1 | 4/2004 | Hollars | |
| 2004/0084080 A1 | 5/2004 | Sager et al. | |
| 2004/0144419 A1 | 7/2004 | Fix et al. | |
| 2004/0214001 A1 | 10/2004 | Oldenburg et al. | |
| 2004/0219730 A1 | 11/2004 | Basol | |
| 2004/0250848 A1 | 12/2004 | Sager et al. | |
| 2005/0022747 A1 | 2/2005 | Stanbery | |
| 2005/0035983 A1 | 2/2005 | Cruchon-Dupeyrat et al. | |
| 2005/0058587 A1 | 3/2005 | Wagner | |
| 2005/0098204 A1 | 5/2005 | Roscheisen et al. | |
| 2005/0150789 A1 | 7/2005 | Crane | |
| 2005/0175836 A1 | 8/2005 | Kuehnle et al. | |
| 2005/0183767 A1 * | 8/2005 | Yu et al. | 136/263 |
| 2005/0183768 A1 | 8/2005 | Roscheisen et al. | |
| 2005/0186342 A1 | 8/2005 | Sager et al. | |
| 2005/0186805 A1 | 8/2005 | Stanbery | |
| 2005/0194036 A1 | 9/2005 | Basol | |
| 2005/0194038 A1 | 9/2005 | Brabec et al. | |
| 2005/0202589 A1 | 9/2005 | Basol | |
| 2005/0235869 A1 | 10/2005 | Cruchon-Dupeyrat et al. | |
| 2005/0247340 A1 | 11/2005 | Zeira | |
| 2005/0266600 A1 | 12/2005 | Basol | |
| 2005/0268962 A1 | 12/2005 | Gaudiana et al. | |
| 2005/0272263 A1 | 12/2005 | Brabec et al. | |
| 2006/0054506 A1 | 3/2006 | Natan et al. | |
| 2006/0062902 A1 * | 3/2006 | Sager et al. | 427/74 |
| 2006/0099146 A1 | 5/2006 | Chow et al. | |
| 2006/0121701 A1 | 6/2006 | Basol | |
| 2006/0134505 A1 | 6/2006 | Wang et al. | |
| 2006/0159922 A1 | 7/2006 | O'Keefe | |
| 2006/0165911 A1 | 7/2006 | Basol | |
| 2006/0178012 A1 | 8/2006 | Basol | |
| 2006/0189155 A1 | 8/2006 | Basol | |
| 2006/0192955 A1 | 8/2006 | Jorgenson et al. | |
| 2006/0207644 A1 | 9/2006 | Robinson et al. | |
| 2006/0251874 A1 | 11/2006 | McClure et al. | |
| 2007/0044834 A1 | 3/2007 | Berke et al. | |
| 2007/0092648 A1 | 4/2007 | Duren et al. | |
| 2007/0093006 A1 | 4/2007 | Basol | |
| 2007/0093059 A1 | 4/2007 | Basol | |
| 2007/0111367 A1 | 5/2007 | Basol | |
| 2007/0145507 A1 | 6/2007 | Basol | |
| 2007/0163383 A1 | 7/2007 | Van Duren et al. | |
| 2007/0163637 A1 | 7/2007 | Robinson et al. | |
| 2007/0163638 A1 | 7/2007 | Van Duren et al. | |
| 2007/0163639 A1 | 7/2007 | Robinson et al. | |
| 2007/0163640 A1 | 7/2007 | Van Duren et al. | |
| 2007/0163642 A1 | 7/2007 | Van Duren et al. | |
| 2007/0163643 A1 | 7/2007 | Van Duren et al. | |
| 2007/0163644 A1 | 7/2007 | Van Duren et al. | |
| 2007/0166453 A1 | 7/2007 | Van Duren et al. | |
| 2007/0166964 A1 | 7/2007 | Basol | |
| 2007/0169809 A1 | 7/2007 | Van Duren et al. | |
| 2007/0169810 A1 | 7/2007 | Van Duren et al. | |
| 2007/0169811 A1 | 7/2007 | Van Duren et al. | |
| 2007/0169812 A1 | 7/2007 | Robinson et al. | |
| 2007/0169813 A1 | 7/2007 | Robinson et al. | |
| 2007/0178620 A1 | 8/2007 | Basol | |
| 2008/0051122 A1 | 2/2008 | Fisher | |
| 2008/0121277 A1 | 5/2008 | Robinson et al. | |
| 2008/0124831 A1 | 5/2008 | Robinson et al. | |
| 2008/0135099 A1 * | 6/2008 | Yu et al. | 136/264 |
| 2008/0135811 A1 * | 6/2008 | Yu et al. | 252/501.1 |
| 2008/0135812 A1 * | 6/2008 | Yu et al. | 252/501.1 |
| 2008/0138501 A1 * | 6/2008 | Yu et al. | 427/74 |
| 2008/0142072 A1 * | 6/2008 | Yu et al. | 136/252 |
| 2008/0142080 A1 * | 6/2008 | Yu et al. | 136/263 |
| 2008/0142081 A1 * | 6/2008 | Yu et al. | 136/264 |
| 2008/0142082 A1 * | 6/2008 | Yu et al. | 136/264 |
| 2008/0142083 A1 * | 6/2008 | Yu et al. | 136/264 |
| 2008/0142084 A1 | 6/2008 | Yu et al. | |
| 2008/0149176 A1 * | 6/2008 | Sager et al. | 136/262 |
| 2008/0213467 A1 * | 9/2008 | Yu et al. | 427/74 |
| 2008/0280030 A1 | 11/2008 | Van Duren et al. | |
| 2008/0305269 A1 * | 12/2008 | Sager et al. | 427/383.3 |
| 2009/0260670 A1 | 10/2009 | Li | |
| 2010/0267189 A1 * | 10/2010 | Yu et al. | 438/95 |

FOREIGN PATENT DOCUMENTS

| | | |
|---|---|---|
| EP | 793277 | 9/1997 |
| JP | 61244004 | 10/1986 |
| JP | 6289369 | 4/1987 |
| JP | 63249379 | 10/1988 |
| JP | 2001044464 | 2/2001 |
| KR | 2005119705 | 12/2005 |
| WO | 02084708 A2 | 10/2002 |
| WO | 03007386 A1 | 1/2003 |
| WO | 03043736 A | 5/2003 |

OTHER PUBLICATIONS

U.S. Appl. No. 12/095,463, filed on May 29, 2008 titled "Chalcogenide Solar Cell".

Weng and Cocivera, Preparation of copper indium diselenide by selenization of copper indium oxide, Journal of Applied Physics, Aug. 1, 1993, 2046-2052, vol. 74, No. 3, American Institute of Physics, New York.

Zhu et al., General Sonochemical Method for the Preparation of Nanophasic Selenides: Synthesis of ZnSe Nanoparticles, Chem. Mater 2000, 12, 73-78.

Office Action dated Aug. 25, 2010 for U.S. Appl. No. 11/933,400.
Office Action dated Aug. 28, 2008 for U.S. Appl. No. 11/361,688.
Office Action dated Dec. 12, 2008 for U.S. Appl. No. 11/361,515.
Office Action dated Dec. 23, 2008 for U.S. Appl. No. 11/395,438.
Office Action dated Dec. 23, 2008 for U.S. Appl. No. 11/395,668.
Office Action dated Dec. 24, 2008 for U.S. Appl. No. 11/361,522.
Office Action dated Dec. 26, 2008 for U.S. Appl. No. 11/361,523.
Office Action dated Dec. 31, 2007 for U.S. Appl. No. 10/782,017.
Office Action dated Feb. 2, 2011 for U.S. Appl. No. 11/933,357.
Office Action dated Feb. 9, 2009 for U.S. Appl. No. 11/395,426.

Office Action dated Feb. 18, 2010 for U.S. Appl. No. 11/933,400.
Office Action dated Feb. 25, 2009 for U.S. Appl. No. 11/361,521.
Office Action Dated Jan. 19, 2011 for U.S. Appl. No. 11/933,338.
Office Action dated Jan. 29, 2009 for U.S. Appl. No. 11/361,103.
Office Action dated Jan. 29, 2009 for U.S. Appl. No. 11/361,498.
Office Action dated Jan. 7, 2009 for U.S. Appl. No. 11/290,633.
Office Action dated Jul. 15, 2008 for U.S. Appl. No. 11/361,433.
Office Action dated Jul. 29, 2008 for U.S. Appl. No. 11/362,266.
Office Action dated Jul. 31, 2008 for U.S. Appl. No. 11/933,375.
Office Action dated Jun. 10, 2009 for U.S. Appl. No. 11/395,668.
Office Action dated Jun. 11, 2008 from U.S. Appl. No. 10/836,307.
Office Action dated Jun. 15, 2009 for U.S. Appl. No. 11/395,438.
Office Action dated Mar. 10, 2009 U.S. Appl. No. 11/361,497.
Office Action dated May 4, 2011 for U.S. Appl. No. 11/933,255.
Office Action dated May 14, 2008 from U.S. Appl. No. 11/081,163.
Office Action dated May 23, 2011 for U.S. Appl. No. 11/933,285.
Padhi et al., Planarization of Copper Thin Films by Electropolishing in Phoshoric Acid for ULSI Applications, Journal of the Electrochemical Society, 2003, G10-G14, vol. 150, No. 1, Electrochemical Society Inc: USA.
Poloni et al., Liquid gallium in confined droplets under high-temperature and high-pressure conditions, Physical Review B 71. 184111 (2005).
Raffaelle et al., Electrodeposited CuInSe(2) thin film junctions, Prepared for the 1997 Fall meeting sponsored by the Materials Research Society, Dec. 1-5, 1997, Boston, MA.
Ramakrishna Reddy et al., Photoacousstic spectroscopy of sprayed $CuGa(x)In(1-x)Se(2)$ thin films, Thin Solid Films, 2001, 205-207, vol. 387, Elsevier Science, Amsterdam: Netherlands.
Saltman and Nachtrieb, The Electrochemistry of Gallium, Journal of the Electrochemical Society, Mar. 1953, 126-130, vol. 100, No. 3, Electrochemical Society Inc.: USA.
Schnable and Javes, Electrodeposition of Molten Low-Melting Metals and Alloys from Fused-Salt Systems, Electrochemical Technology, Jul.-Aug. 1964, 201-206, Electrochemical Society, Manchester, N. H.
Schnable, Electrodeposition of Molten Metals and Alloys from Glycerine Solutions, Journal of the Electrochemical Society, Oct. 1961, 964-969, vol. 108, No. 10, Electrochemical Society Inc.: USA.
Schulz et al., Cu-In-Ga-Se Nanoparticle Colloids as Spray Deposition Precursors for Cu(in, Ga)Se(2) Solar Cell Materials, Journal of Electornic Materials, 1998, 433-437, vol. 27, No. 5, Mineral Metals & Materials Society: USA.
Schwarcz et al., TEM observations of early nucleation and growth stages in aluminum films on liquid gallium droplets, Thin Solid Films (1994), 245(1-2), 260-6.
Sen et al., "Preparation of Cu, Ag, Fe and Al nanoparticles by the exploding wire technique" in Proc. Indian Acad. Sci. (Chem. Sci.), vol. 115, nos. 5 & 6, pp. 499-508, Oct.-Dec. 2003, Indian Academy of Sciences.
U.S. Appl. No. 11/396,199, filed on Mar. 30, 2006 titled "Dispersion Using Inter-metallic Materials".
U.S. Appl. No. 11/290,633, filed on Mar. 15, 2005, titled "Metallic Dispersion".
U.S. Appl. No. 11/933,136, filed on Oct. 31, 2007 titled "Solution-based Fabrication of Photovoltaic Cell".
U.S. Appl. No. 11/933,255, filed on Oct. 31, 2007 titled "Solution-based Fabrication of Photovoltaic Cell".
U.S. Appl. No. 11/933,285, filed on Oct. 31, 2007 titled "Solution-based Fabrication of Photovoltaic Cell".
U.S. Appl. No. 11/933,315, filed on Oct. 31, 2007 titled "Solution-based Fabrication of Photovoltaic Cell".
U.S. Appl. No. 11/933,322, filed on Oct. 31, 2007 titled "Solution-based Fabrication of Photovoltaic Cell".
U.S. Appl. No. 11/933,338, filed on Oct. 31, 2007 titled "Solution-based Fabrication of Photovoltaic Cell".
U.S. Appl. No. 11/933,357, filed on Oct. 31, 2007 titled "Solution-based Fabrication of Photovoltaic Cell".
U.S. Appl. No. 11/933,375, filed on Oct. 31, 2007 titled "Solution-based Fabrication of Photovoltaic Cell".
U.S. Appl. No. 11/933,400, filed on Oct. 31, 2007 titled "Solution-based Fabrication of Photovoltaic Cell".

Arita et al., CuInSe(2) films prepared by screen-printing and sintering method, 1988, IEEE.
B. A. Ridley et al, "All-Inorganic Field Effect Transistors Fabricated by Printing" in Science, vol. 286, pp. 746-749, Oct. 22, 1999.
Banger et al., "Synthesis and Characterization of the First Liquid Single-Source Precursors for the Deposition of Ternary Chalcopyrite (CuInS2) Thin Film Materials", Chem Matter, vol. 13, 3827-3829, 2001, American Chemical Society.
Beck, and Michael Cocivera, Thin-film copper indium diselenide prepared by selenization of copper indium oxide formed by spray pyrolysis, Thin Solid Films, 1996, 71-82, vol. 272, Elsevier Publishing Company, Amsterdam.
Berty et al., Electron diffraction study of the supercooling of very small gallium droplets, Scripta Metallurgica (1976), 10(7), 645-8.
Bosio and Windsor, Observation of a Metastability Limit in Liquid Gallium, Physical Review Letters, vol. 35, No. 24, Dec. 15, 1975.
Carmalt et al., Solid-state and solution phase metathetical synthesis of copper indium chalcogenides, Journal of Materials Chemistry, 1998, 2209-2211, vol. 8, No. 10, Roya Society of Chemistry, Great Britain.
Castro et al., "Nanocrystalline Chalcopyrite Materials (CuInS2 and CuInSe2) via Low-Temperature Pyrolsis of Molecular Single-Source Precursors" Chem Mater, vol. 15, pp. 3142-3147, 2003.
De Silva et al., Electrodeposition and characterization of CuInSe(2) for applications in thin film solar cells, Thin Solid Films, 2001, 158-163, vol. 382, Elsevier Science, Amsterdam: Netherlands.
Di Cicco et al., Phase transitions and undercooling in confied gallium, Philosophical Magazine B: Physics of Condensed Matter: Statistical Mechanics, Electronic, Optical and Magnetic Properties (1999), 79(11/12), 2113-2120. Publisher: Taylor & Francis Ltd.
Di Cicco, Phase Transitions in Confined Gallium Droplets, Physical Review Letters (1998), 81(14), 2942-2945, Publisher: American Physical Society.
Eberspacher et al., Non-vacuum processing of CIGS solar cells, UNISUN, 223-224, 2001, Newbury Park, CA.
Eberspacher et al., Non-vacuum processing of CIGS solar cells, UNISON, pp. 1-5, 2003, Newbury Park, CA.
Eberspacher et al., Non-vacuum thin-film CIGSs modules, Materials Research Society Symposia Proceedings, 2003, B8.27.1-B8.27.6, vol. 763, Materials Reserach Society, Warrendale, PA.
Eberspacher et al., Thin-filme CIS alloy PV materials fabricated using non-vacuum, particles-based techniques, Thin Solid Films, 2001, 18-22, Volumer 387, Elsevier Publishing Company, Amsterdam.
Freeman et al., Ag-Clad Au Nanoparticles: Novel Aggregation, Optical, and Surface-Enhanced Raman Scattering Properties, J. Phys. Chem., vol. 100, 1996, pp. 718-724.
Guillen and Herrero, Recrystallization and components redistribution processes in electrodeposited CuInSe(2) thin films, Thin Solid Films, 2001, 57-59, vol. 387, Elsevier Science, Amsterdam: Netherlands.
Heyding et al., Metastable phases in gallium dispersions, Journal of Physics and Chemistry of Solids (1973), 34(1), 133-6.
Huang et al., Preparation and internal friction of nanoscale gallium droplets, Physica Status Solidi A: Applied Research (2002), 194(1), 167-172.
ISET, Inc. Website (isetinc.com/cigs.html) from Feb. 4, 2003, available from www.archive.org, 2 pages.
Kaelin et al., CIS and CIGS layers from selenized nanoparticle precursors, Thin Solid Films, 2003, 58-62, vol. 431-432, Elsevier Science, Amsterdam: Netherlands.
Kaelin et al., Electrosprayer and selenized Cu/In metal particle films, Thin Solid Films, 2004, 391-396, vol. 457, Elsevier Science, Amsterdam: Netherlands.
Kampmann et al., Juction Formation Studies of One-Step Electrodeposited CuInSe(2) on CdS, Journal of The Electrochemical Society, 1999, 150-155, vol. 146, No. 1, Royal Society of Chemistry, Great Britain.
Kapur et al., Non-Vacuum Processing of $CuIn(1-x)Ga(x)Se(2)$ solar cells on rigid and felixble substrates using nanoparticle precursor inks, Thin Solid Films, 2003, 53-57, vol. 431-432, Elsevier Publishing Company, Amsterdam.

Karpov et al., Gallium droplet formation during MOVPE and thermal annealing of GaN, Materials Science & Engineering, B: Solid-State Materials for Advanced Technology (2001), B82(1-3), 22-24.

Kemell et al., Electrochemical Quartz Crystal Microbalance Study of the Electrodeposition Mechanisms of CuInSe(2) Thin Films, Journal of The Electrochemical Society, 2001, C110-C118, vol. 148, No. 2, Electrochemical Society: USA.

Kronik et al., "Interface redox engineering of Cu(in,Ga)Se2-based solar cells: oxygen, sodium, and chemical bath effects", Thin Solic Films, vol. 361-362, p. 353-359 (2000).

Lee et al., Fabrication of high-output-power AlGaN/GaN-based UV-light emitting diode using a Ga droplet layer, Japanese Journal of Applied Physics, Part 2: Letters (2002), 41(10A), L1037-L1039.

Li et al, "Synthesis by a Solvothermal Route and Characterization of CuInSe2 Nanowhiskers and Nanoparticles" in Advanced Materials, vol. 11, no. 17, pp. 1456-1459, 1999, Wiley-VCH Verlag GmbH.

Miyazawa and Pound, Homogeneous Nucleation of Crystalline Gallium from Liquid Gallium, Journal of Crystal Growth 23 (1974) 45-57.

Munoz et al., Electrodeposition of Indium onto Vitreous Carbon from Acid Chloride Solutions, Journal of The Electrochemical Society, 1999, 2123-2130, vol. 146, No. 6, Electrochemical Society Inc.: USA.

Norsworthy et al., CIS film growth by metallic ink coating and selenization, Solar Energy Materials & Solar Cells, 2000, 127-134, vol. 60, Elsevier Science, Amsterdam: Netherlands.

Notice of Allowance and Fees dated Aug. 31, 2011 for U.S. Appl. No. 11/933,400.

Notice of Allowance and Fees dated Jul. 11, 2008 for U.S. Appl. No. 10/782,017.

Notice of Allowance and Fees dated Jul. 13, 2011 for U.S. Appl. No. 11/933,338.

Notice of Allowance and Fees dated Mar. 20, 2009 for U.S. Appl. No. 10/783,017.

Notice of Allowance and Fees dated Nov. 28, 2011 for U.S. Appl. No. 10/782,017.

Notice of Allowance and Fees dated Oct. 18, 2011 for U.S. Appl. No. 11/933,285.

Notice of Allowance and Fees dated Sep. 18, 2009 for U.S. Appl. No. 10/782,017.

Office Action dated Apr. 1, 2009 for U.S. Appl. No. 11/933,400.
Office Action dated Apr. 5, 2007 for U.S. Appl. No. 10/836,307.
Office Action dated Apr. 10, 2009 for U.S. Appl. No. 11/362,266.
Office Action dated Apr. 14, 2011 for U.S. Appl. No. 11/933,400.
Office Action dated Apr. 28, 2011 for U.S. Appl. No. 11/933,407.
Office Action dated Aug. 4, 2011 for U.S. Appl. No. 11/933,383.
Office Action dated Aug. 22, 2011 for U.S. Appl. No. 11/933,357.

* cited by examiner

SOLUTION-BASED FABRICATION OF PHOTOVOLTAIC CELL

CROSS-REFERENCE TO RELATED APPLICATION

This application is a continuation of U.S. patent application Ser. No. 10/782,017 filed Feb. 19, 2004 now U.S. Pat. No. 7,663,057. This application is also related to commonly-assigned application Ser. No. 10/782,545, titled "HIGH THROUGHPUT SURFACE TREATMENT ON COILED FLEXIBLE SUBSTRATES" filed Feb. 19, 2004 now U.S. Pat. No. 7,115,304. Both applications are fully incorporated herein by reference for all purposes.

FIELD OF THE INVENTION

This invention is related to photovoltaic cells and more particularly to fabrication of IB-IIIA-VIA active layers for such cells.

BACKGROUND OF THE INVENTION

Low-cost production of solar cells on flexible substrates using printing or web coating technologies is promising highly cost-efficient alternative to traditional silicon-based solar cells. Recently, solution-based solar cells fabricated from alloys of copper (Cu) and indium (In) with selenium (Se) or sulfur (S) have been developed. Such CIGS solar cells have been fabricated using a non-vacuum process in which a water-based precursor ink is formulated containing mixed oxides of Cu, In and Ga, which is then coated on rigid or flexible substrates (see U.S. Pat. No. 6,127,202, issued October 2000 to Kapur et. al., and U.S. Pat. No. 6,268,014 issued July 2001 to Eberspacher and Pauls). The resulting oxide mixture was then subject to reduction in $H_2/N_2$ mixture and selenization in an $H_2Se/N_2$ mixture at high temperatures between 400 to 500° C. The resulting CIGS solar cells typically have efficiency in the range of 8 to 11%. Another alternative ink-based approach used metallic powder paste to coat on substrates followed by selenization under $H_2Se/N_2$ at high temperature to form a CIS (or CIGS cell) solar cell (Kapur, V. K., et. al. *Sol. Energy Mater Sol. Cells*, 60 (2000) 127-134 and Kapur et al, *Thin Solid Films*, 431-432 (2003) 53-57 and also Kaelin, M., Meyer, T., Kurdesau, F., Rudmann, D., Zogg. H. and A. N. Tiawri. Low Cost Cu(In, Ga)Se$_2$ Absorber Layers from Selenization of Precursor Materials, 3rd World Conference on Photovoltaic Energy Conversion, Osaka, Japan, 2003). Unfortunately, the high temperature reduction and selenization steps used in each of these solar cell fabrication processes are neither cost effective nor easily scaled to high-volume production. Specifically, the $H_2Se$ gas used is both highly toxic and flammable. Thus, when $H_2Se$ is used at high temperatures, safety, environmental impact, and overall cost are serious concerns in the manufacturing process.

Furthermore, the high temperature reduction and selenization steps make it impractical to make CIGS solar cells on inexpensive polymer or metallized polymer substrates that would warp, melt, or otherwise degrade at such high temperatures in the presence of reducing and/or oxidizing agents.

Although it is possible to make CIGS-based inks without using oxides, such inks have been produced in the prior art have several drawbacks for high-volume, roll-to-roll processing. For instance, the use of bulk CuInSe$_2$ as a starting material is challenging as bulk CuInSe$_2$ has a melting point around 1000° C. However, since most of the flexible substrates such as Al foils and plastic foils cannot withstand such a high temperature, it is not possible to melt bulk material directly onto a substrate. Even glass will have serious warping problems at this temperature and substrate warping typically leads to inefficient cell performance—so even with deposition onto glass, it is very difficult to create high-performance solar cells by melting bulk material. Moreover, the energy requirements needed for high temperature manufacturing at 1000° C. will incur substantial cost. Consequently, processes occurring at much lower temperatures are preferred. However, annealing at a lower temperature tends to hinder the manner of crystal grain growth that is critical for the proper electronic properties of CIGS solar cell. Certain fluxing agents have been used to reduce the melting point and sintering temperature for CuInSe$_2$ (A. Vervaet et al. in 9$^{th}$ European Communities PV Solar Energy Conference, 1989, 480). Unfortunately, such fluxing agents can introduce unwanted crystalline phases and alter the electronic properties of CIGS, thus lowering the efficiency of a CIGS solar cell.

Thus, there is a need in the art, for a non-oxide based precursor ink that overcomes the above disadvantages.

BRIEF DESCRIPTION OF THE DRAWINGS

The teachings of the present invention can be readily understood by considering the following detailed description in conjunction with the accompanying drawings, in which.

DESCRIPTION OF THE SPECIFIC EMBODIMENTS

Figure 1:
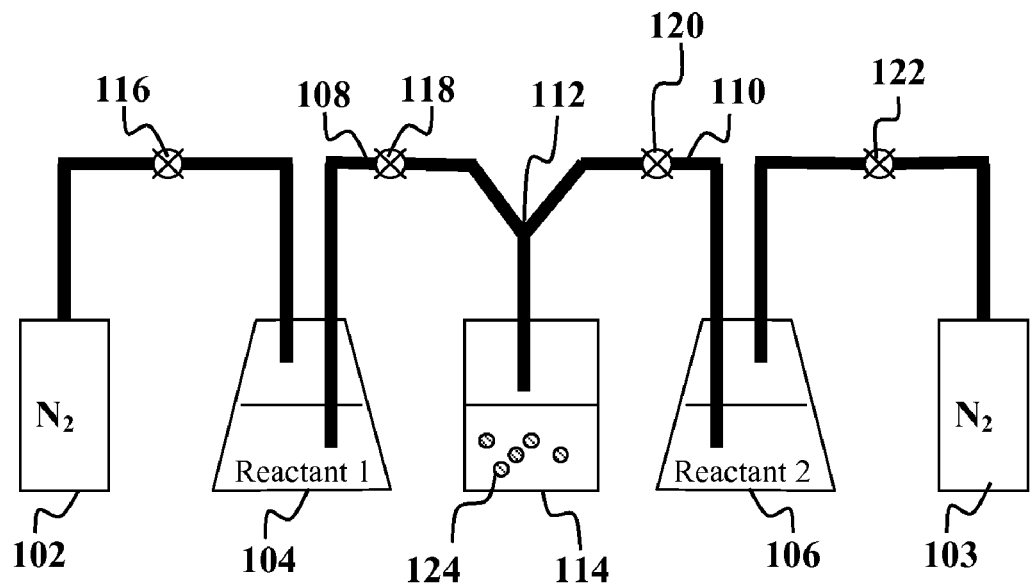
FIG. 1 is a schematic diagram of a spay co-precipitation apparatus for fabrication of nanoparticles according to an embodiment of the present invention.

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

As used herein, the following terms have the following meanings:

"Elemental" refers to a material in substantially pure form as opposed to combined with other elements as in an alloy or in a chemical compound.

"Non-oxide" refers to a chemical moiety substantially devoid of oxygen.

Embodiments of the present invention provide several key features of a liquid ink that impact cell structure and function. The liquid ink includes particles containing elements of groups IB, IIIA and (optionally) VIA, e.g., copper and indium (with or without gallium) and selenium or sulfur. The particles may be between about 0.1 and about 500 nm. The decreased particle size can significantly lower both the melting point and the sintering temperature required (see e.g., C R M Wronski, "*The Size Dependence of the Melting point of Small Particles of Tin*" in the *British Journal of Applied Physics vol.* 18, *No.* 12, (December 1967) pp 1731-1737, IOP Publishing, Bristol, UK; L. H. Allen, "Nanocalorimetry Studies of Materials: Melting Point Depression and Magic Nanostructures" NNUN Abstracts 2002/Materials, Physics, Processes & Characterization, pp 40; Zhang et al., 2000. "Size-dependent melting point depression of nanostructures: Nanocalorimetric measurements." Phys. Rev. B 62 (15): 548-

557; Lisecki et al. 2000. "Annealing Process of Anisotropic Copper Nanocrystals." 2. Rods. Langmuir 16: 8807-8808). Generally, reduction in the melting point is inversely proportional to the particle radius, i.e., the smaller the nanoparticles, the lower the melting point. Smaller particles also tend to pack closer together and make better contact with each other. Reduction in size from bulk material to particles in about the 500 nm regime can already show significant differences in melting point and other altered physical and chemical properties. With much smaller particle sizes, e.g. in the nanometer size range, the surface area of particles will increase and nanoparticles will be in intimate contact with each other. In addition, in the nanometer size range, the reactivity of the particles and interaction between nanoparticles will be enhanced. This will help particles fuse together much easier thus enhancing the cohesion of the resulting CIGS layer (W. H. Qi, et al. in "China—EU Forum on Nanosized Technology" Beijing, P.R. China. December 2002. pp 86-92). This promotes coalescence between neighboring particles during sintering.

The particle sizes in the ink are typically distributed over a relatively narrow range, e.g. with the majority of particles of a given type being within about 40% of an average particle size for that type. Note that for an ink containing particles of different chemical types, e.g., different elemental metals, or different binary combinations, the different types of particles may have different average sizes so that the particles in the ink all melt at about the same temperature. By appropriately adjusting the particle size distribution amongst the particles of different materials in the mixture, it is possible for all the particles to melt at about the same temperature during sintering and yield more uniform crystalline phases. This enhances the electronic properties of the crystals in the resulting CIGS film. By contrast, in the prior art, $CuInSe_2$ powders generated, e.g., by a milling or nebulizing process to create powder precursors have typically contained a mixture of both small and large particles, resulting in a relatively broad size distribution. The presence of such a broad size distribution results in poor film formation. In particular, smaller particles tend to melt first while big particles remain unmelted. Further, particles of different sizes can non-uniformly distribute within a film. This heterogeneity leads to defects in film growth, decreases the uniformity and size of crystal grains, and negatively impacts the electronic properties (e.g., resistivity, bandgap, and carrier transport) of the CIGS layer upon incorporation into a photovoltaic device such as a solar cell. Although the prior art has addressed the advantages of a smaller average particle size in IB-IIIA-VI nanoparticle inks (see e.g., U.S. Pat. No. 6,126,740 to Schulz), the resulting active layers made by annealing such inks have often been of relatively poor quality. The inventors have recognized that the problem is not just the particle size but also the particle size distribution, an issue that Schultz does not address.

Therefore, according to embodiments of the present invention, an ink for forming an active layer for a photovoltaic cell can be fabricated by forming liquid containing nanoparticles (e.g., elemental metal nanoparticles, non-oxide quantum nanoparticles, or metallic nanoparticles) of about 0.1-nm to about 500-nm diameter containing elements from groups IB, IIIA and VIA. A film of the ink can be spread onto a substrate, and annealed to form a layer of IB-IIIA-VIA material. The nanoparticles may have a narrow size distribution characterized by an average nanoparticle size D. For example, the nanoparticles used to make up the film may have sizes within about 40% of D. If the average particle size is less than about 5 nm, then the variation can be bigger, e.g., between about 1 nm and about 2 nm.

In this case, the resulting range of melting points is still sufficiently small to be considered to have a narrow particle size distribution. By way of example, the particles in the liquid may include Cu with In or Ga and Se or S in a stoichiometric ratio of approximately $CuIn_{1-x}Ga_x(S, Se)_2$, where x is between 0 and 1.

Quantum nanoparticles are an important class of nanoparticles that can be used to make inks according to embodiments of the present invention. The electronic and optical properties of metals and semiconductors can change dramatically as the particulates of the materials are reduced to approach the nanometer size range of dimensions. At such size levels, the physical dimensions of the material generally impact the electronic, optical, chemical, and/or physical behavior of the material. The restriction of an electronic wave function to smaller and smaller regions of space within a particle of material (the resonance cavity) is referred to as "quantum confinement". Metal or semiconductor structures in the nanometer size range, exhibiting the characteristics of quantum confinement, are commonly referred to as "quantum dots" when the confinement is in three dimensions, "quantum wires" or "quantum rods" when the confinement is in two dimensions, and "quantum wells" when the confinement is in one dimension.

Quantum nanoparticles generally form in a size regime where the average particle diameter is less than about 10 nm. This small size results in new quantum phenomena that can change dramatically relative to a corresponding bulk material in part because quantum effects arise from the confinement of electrons and "holes" in the material (a hole represents the absence of an electron; the hole behaves as though it were a positively charged particle). The small particle size also changes other material properties, such as the electrical and nonlinear optical properties of a material, making them very different from those of the material's bulk form. For example, the optical bandgap of a quantum nanoparticle can often differ significantly from that of the material's bulk form. Further, the increased surface area to volume ratio of quantum nanoparticles renders them more reactive than the material's bulk form, often resulting for example in a dramatic melting point depression.

It should also be understood that group IB, IIIA, and VIA elements other than Cu, In, Ga, Se, and S may be included in the description of the IB-IIIA-VIA alloys described herein, and that the use of a hyphen ("-" e.g., in Cu—Se or Cu—In—Se) does not indicate a compound, but rather indicates a coexisting mixture of the elements joined by the hyphen. Where several elements can be combined with or substituted for each other, such as In and Ga, or Se, and S, in embodiments of the present invention, it is not uncommon in this art to include in a set of parentheses those elements that can be combined or interchanged, such as (In, Ga) or (Se, S). The descriptions in this specification sometimes use this convenience. Finally, also for convenience, the elements are discussed with their commonly accepted chemical symbols. Group IB elements suitable for use in the method of this invention include copper (Cu), silver (Ag), and gold (Au). Preferably the group IB element is copper (Cu). Group IIIA elements suitable for use in the method of this invention include gallium (Ga), indium (In), aluminum (Al), and thallium (Tl). Preferably the group IIIA element is gallium (Ga) or indium (In). Group VIA elements of interest include selenium (Se), sulfur (S), and tellurium (Te), and preferably the group VIA element is either Se or S.

A nanoparticle-based CIGS ink has great utility for low cost web coating of ink-based photovoltaic cells. Methods to make nanoparticles of the desired materials having the desired narrow particle size distribution include controlling the reaction conditions under which the nanoparticles are made or using size-selective precipitation and other techniques (such as ultrafiltration and membrane emulsification). Nanoparticles in different categories may be incorporated into CIGS inks. These categories include but are not limited to: (1) Ternary nanoparticles such as $CuInSe_2$ or CuInG nanoparticles; (2) Binary nanoparticles such as CuSe and $In_2Se_3$ nanoparticles; (3) Metallic nanoparticles such as Cu and In nanoparticles; (4) A suspension made using one or more liquid metals, such as Ga; (5) A liquid made using one or more organometallic precursors. Significantly, each of these approaches may be implemented without selenization of the particles, film or IB-IIIA-VIA layer using $H_2Se$; (6) Metal halides dissolved in chelating agents; and (7) Metal salts. All of these techniques may be used to form a liquid ink. In addition, the use of non-oxide or elemental metal particles avoids having to reduce the particles, film or IB-IIIA-VIA layer with $H_2$.

The following examples illustrate several different ways, among others for creating nanoparticles with a narrow size distribution in the desired size range.

1. Ternary IB-IIIA-VIA Non-Oxide Quantum Nanoparticles (e.g., $Cu(In, Ga)Se(S)_2$)

According to one set of embodiments of the present invention, ternary, non-oxide quantum nanoparticles (e.g., quantum dots or quantum rods) for making a IB-IIIA-VIA ink may be fabricated by several different approaches.

1.1 Preparation of Organic Capped $CuInSe_2$ Non-Oxide Quantum Nanoparticles

Non-oxide quantum nanoparticles of $CuInSe_2$ may be fabricated according to a chemical reaction of the type:

$$(IB)(Hal)+(IIIA)(Hal)+TOP(VIA)+TOPO \rightarrow IB\text{-}IIIA\text{-}VIA,$$

where IB refers to an element of group IB, IIIA refers to an element of group IIIA, VIA refers to an element of group VIA and Hal refers to a halogen, preferably iodine (I) or chlorine (Cl). By way of example, IB can be Cu, IIIA can be Ga or In and VIA can be Se or S. In a particular example, among others, the reaction may be of the form:

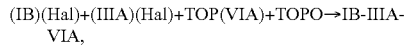

The size distribution of the particles may be adjusted by controlling the reaction conditions under which the nanoparticles are made. By way of example, Trioctylphosphine oxide (TOPO) (20 g) may be heated to about 100° C., followed by degassing and flushing with nitrogen. An equimolar solution of $InCl_3$ (2.20 g, 0.01 mol) and CuCl (1.0 g, 0.01 mol) in Trioctylphosphine (TOP) (15 mL) is injected into the hot TOPO at 100° C. The colorless TOPO turned bright yellow after injection, and the temperature drops to 80° C. The reaction may proceed for about 30 min to one hour, after which the temperature is increased to 250° C., and then 1.0 M trioctylphospine selenide (TOPSe) (20 mL) is injected into the TOPO solution (a mixture of Se powder (1.66 g) and TOP (20 mL) is stirred at room temperature for 48 h to give a clear solution (1 M) of TOPSe. There may be an initial drop in temperature to 220° C., after which the reaction stabilizes at about 250° C. and proceeds for 24-36 h. The reaction mixture is then cooled to about 60° C., followed by the addition of excess methanol to flocculate the particles. There may be no immediate visible precipitation on the addition of methanol. A fine precipitate typically appears after stirring overnight. The precipitate may be separated by centrifugation and washed with methanol to remove the excess TOPO and then dissolved in toluene. (See e.g., M. A. Malik et. al. *Adv. Mater.* 1999, 11(17), 1441). Nanoparticles in the desired size distribution may be obtained from the precipitate, e.g., by size-selective precipitation or ultrafiltration. TOPO-capped $CuInSe_2$ nanoparticles may be mixed with water and an optional dispersant in an aqueous liquid to form a CIGS ink. The ratio of nanoparticles to water in weight percentage may be between about 10% and about 60%, e.g. about 40%. After coating a substrate with a film of the ink, the TOPO may be decomposed when heated at elevated temperature. At the same time, $CuInSe_2$ nanoparticles sinter together to form a polycrystalline film.

1.2 Preparation of $CuInSe_2$ Non-Oxide Quantum Nanoparticles with a Volatile Capping Agent TOPO is a relatively large organic molecule, and since it can be difficult to completely remove large molecules like TOPO by simple thermal decomposition, so carbon contamination can be a potential issue in device fabrication. To overcome this disadvantage, a more preferred embodiment uses a smaller molecule with a lower boiling point, such as pyridine, as a coordinating ligand and solvent. In prior art, pyridine has been demonstrated to retard nanoparticle growth and narrow the size distribution in the case of CdSe nanoparticles. In that prior art, pyridine loosely caps the nanoparticles and ripens the nanoparticles continuously. This same principle can be applied to CIGS nanoparticles, which may be fabricated according to a reaction of the type:

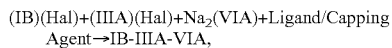

where IB, IIIA, VIA and Hal have the meanings described above. As used herein, a capping agent can be broadly defined as a compound that binds to metal. General classes of ligands/capping agents include, but are not limited to phosphines, amines, alcohols, thiols, ethers, water, and glycols. By way of example, the ligand/capping agent can be pyridine, trioctylphosphine oxide (TOPO), trioctylphosphine sulfide, trioctylphosphine selenide, trioctylphosphine (TOP), triphenylphosphine, pyridine, alcohols (methanol, ethanol, propanol, butanol), thiols, ethane thiol, tetrahydrofuran, ethers, ammonia, amines (methyl amine, ethylamine, ethanolamine, ethylenediamine, trioctyl amine), ethylenediaminetetraacetic acid (EDTA), glycols, amines, diketonates, carboxylic acids, and/or acetonitrile. In a preferred embodiment, the ligand/capping agent is pyridine.

By way of example, the reaction may be of the type:

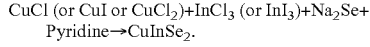

By way of example, and without limitation, CuCl (or CuI or $CuCl_2$) and $InCl_3$ (or $InI_3$) with a Cu/In molar ratio ranging from 0.8 to 1.0 may be mixed in alcohol (methanol or ethanol). The concentrations for Cu and In ions may range from about 5 to 10 mM. $Na_2Se$ may also be prepared in alcohol with a concentration double that of the Cu ions. The two alcoholic solutions are then added into a round-bottom reaction flask with pyridine. The precipitated nanoparticles are collected by filtration or centrifugation. The nanoparticles are then washed with organic solvents and redissolved in pyridine. The resulting $CuInSe_2$ nanoparticles are nanometer in size, with a narrow particle size distribution. Since pyridine is volatile, upon heating the coated film made from this nanoparticle ink has carbon-free nanocrystals, with minimal carbon contamination. Further sintering and annealing at lower temperature yields crystalline grains with uniform phases. (see e.g., B. A. Ridley et. al. *Science,* 1999, 286, 746).

1.3. Preparation of Non-Oxide Quantum Nanoparticles from Single-Source Precursors In other embodiments of the present invention, ternary IB-IIIA-VIA nanoparticles may be prepared from single-source precursors. For instance, CuInS$_2$ nanoparticles may be prepared using the precursor (PPh$_3$)$_2$CuIn(SEt)$_4$. By way of example, dioctyl phthalate (10 mL) may be heated to about 125° C. under vacuum for about 1 h to dry and degas the solvent. The flask may be back-filled with argon and cooled to room temperature prior to adding the precursor. (PPh$_3$)$_2$CuIn(SEt)$_4$ (2.0 g, 2.0 mmol) is then added to the reaction flask and heating is resumed. At approximately 150° C. the precursor dissolved to form a transparent yellow solution. Typically, no further change is observed with time at this temperature. At about 150° C., the precursor remains, for the most part, intact.

Upon increase of the temperature to about 200° C. a red powder begins to precipitate within a few minutes. A reaction time of about 2-3 hours may be employed to complete the precipitation and maximize the yield. After cooling to room temperature under argon, toluene (40 ml) may be added to the reaction mixture to lower the viscosity of the reaction mixture and the red powder may be isolated by centrifugation. The powder may be consecutively washed with toluene and then methanol to remove any reaction byproducts and unreacted starting material, and then dried under vacuum at about 60-80° C. The washing and centrifugation steps may be carried out in ambient atmosphere. Then the product may be collected and stored in a nitrogen-filled glovebox. A portion of the product (100 mg) may be placed in a flask containing fresh dioctyl phthalate (10 mL), heated to higher temperatures, e.g. 250 to 300° C., and held at that temperature for about 1 hour. At a temperature of about 250° C., a brown/black powder (CuInS$_2$) is obtained. At about 300° C. the resulting powder is black and contains a CuInS$_2$ nanoparticulate. (See, e.g., S. L. Castro et. al. *Chem. Mater.* 2003, 15, 3142)

Approximately the same procedure as outlined above may be followed for a CuInSe$_2$ precursor. The precursor may be dissolved in the dioctyl phthalate at 138° C. For example, (PPh$_3$)$_2$CuIn(SePh)$_4$ (1.951 g, 1.47 mmol) may be dissolved in about 10 mL of dioctyl phthalate. A red powder (0.523 g) may be collected after about 2 hours of heating at 200 to 300° C. This power contained a CuInS(Se)$_2$ nanoparticulate.

The size distributions of the CuInS$_2$ or CuIn(Se)$_2$ nanoparticulates may be adjusted by size-selective precipitation, ultrafiltration and the like.

1.4. Preparation of CuInS(Se)$_2$ Nanoparticles Using Spray Co-Precipitation

An alternative embodiment to reduce particle size and narrow the particle size distribution utilizes a spray co-precipitation technique. In the prior art, ZnGa$_2$O$_4$ nanocrystals with a mean particle size less than 10 nm have been made using spray co-precipitation. In a spraying co-precipitation apparatus 100, as shown in FIG. 1, compressed inert gas, e.g., nitrogen from gas sources 102, 103 drives reactants from reactant sources 104, 106 very quickly through stainless steel pipelines 108, 110. The flow rate can be adjusted by a flow-meter from about 5 to about 20 m/s. In general, one of the reactants may include one or more metal salts. As used herein the term metal salts includes metal halides, metal acetates, metal sulfates, metal nitrates, metal alcholates, metal carbonates, metal phenolates and/or organometallics. In a particular example, the reactants may include, a metal halide, such as CuHal/InHal (where Hal refers to I or Cl) and thiourea or selenourea. The reactants mix and react at a T joint 112 of the two pipelines 108, 110 and then spray into a beaker 114 with solvents (e.g., water or alcohols). The molar ratio of Cu, In and thiourea or selenourea may be adjusted e.g., by controlling the flow of the reactants with valves 116, 118, 120, 122 to form CuInS$_2$ nanocrystals 124. The size distributions of the nanocrystals 124 may be adjusted by size-selective precipitation, ultrafiltration and the like. For further information see Z. Jiao et. al. Sensors 2003, 15, 3142.

2. Production of Binary Nanoparticles

Some of the embodiments described above can be modified to produce binary non-oxide quantum nanoparticles, e.g., IB-VIA or IIIA-VIA or IB-VIA nanoparticles. These may be mixed together in the liquid to provide the desired ratios of IB, IIIA and VIA elements. By way of example there are several different approaches to producing CuSe and In$_2$Se$_3$.

2.1. TOPO-Capped CuSe Non-Oxide Quantum Nanoparticles

In another embodiment, quantum dots with nearly uniform size may be fabricated by solvothermal methods according to a reaction of the type:

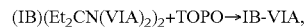
(IB)(Et$_2$CN(VIA)$_2$)$_2$+TOPO→IB-VIA, where IB, IIIA, VIA and TOPO have the meanings describe above. By way of example IB may be Cu, and VIA may be Se or S.

In a particular example, the quantum dots may be fabricated using a reaction of the type:

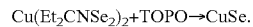
Cu(Et$_2$CNSe$_2$)$_2$+TOPO→CuSe.

Quantum dots and rods of this type have been synthesized in the range of about 5 to about 15 nm using Solvothermal or solution reaction methods (see, e.g., M. A. Malik et. al. "A Novel Route for the Preparation of CuSe and CuInSe$_2$ Nanoparticles," in *Advanced Materials*, Vol 11, No. 17, pp 1441-1444, 1999). By way of example, and without limitation, CuSe Quantum Dots may be fabricated as follows. Cu(Et$_2$CNSe$_2$)$_2$ (0.5 to 2 g) may be dissolved in tri-n-octylphosphine TOP (10 to 30 mL). This solution is then injected into hot tri-n-octylphosphine oxide TOPO (10 to 20 g) at 250° C. A decrease in temperature of 20-30° C. may be observed. The solution is then allowed to stabilize at about 250° C. and is heated for about 60 min at this temperature. The solution is then cooled to approximately 70° C., and after an excess of methanol was added, a flocculant precipitate forms. The solid may be separated by centrifugation, washed with methanol, and redispersed in toluene. The toluene may then be removed under a vacuum to give pale yellow TOPO-capped CuSe nanoparticles. The particles may be washed three times with methanol and redissolved in toluene. Size-selective precipitation may then be carried out on the particles to obtain a collection of quantum dots of the desired average particle size and size distribution.

2.2. CuSe Non-Oxide Quantum Nanoparticles Prepared in Volatile Solvent

Pyridine-capped binary nanoparticles (e.g., CuSe) may be prepared according to a reaction of the type:

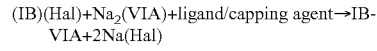
(IB)(Hal)+Na$_2$(VIA)+ligand/capping agent→IB-VIA+2Na(Hal)

By way of example, IB may be Cu, Hal may be Cl or I, VIA may be Se or S. The ligand/capping agent may be any ligand that is co-processable with the metal salts used. By way of example, the ligand/capping agent may be pyridine, trioctylphosphine oxide, trioctylphosphine, triphenylphosphine, pyridine, alcohols (methanol, ethanol, propanol, butanol), ethane thiol, tetrahydrofuran, ethers, ammonia, amines (methyl amine, ethylamine, ethylenediamine) and/or acetonitrile. In a particular example, the reaction may be of the type:

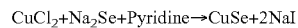
CuCl$_2$+Na$_2$Se+Pyridine→CuSe+2NaI

The conditions for this reaction are similar to those described in section 1.2 except that there is no In ion involved in the reaction.

2.3. $In_2Se_3$ Non-Oxide Quantum Nanoparticles Prepared in Volatile Solvent $In_2Se_3$ nanoparticles may be prepared according to a reaction of the type $$(IIIA)(Hal) + Na_2(VIA) \rightarrow IIIA\text{-}VIA + Na(Hal).$$

Where IIIA, VIA and Hal can be any of the appropriate elements described above. By way of example, the reaction may be of the type $$2InI_3 + 3Na_2Se \rightarrow In_2Se_3 + 6NaI$$

The conditions for this reaction are similar to those described in section 1.2 except that there is no Cu ion involved in the reaction.

2.4. Sonochemical Synthesis of CuSe, $In_2Se_3$ or $CuInSe_2$ Non-Oxide Quantum Nanoparticles In the prior art, ZnSe nanoparticles with a mean size of 3 nanometers have been prepared using a sonochemical method (see, e.g., J. Zhu et. al. *Chem. Mater.* 2000, 12, 73). According to an alternative embodiment of the invention, the same sonochemical method can be applied to forming CuSe or $In_2Se_3$ or $CuInSe_2$ nanoparticles for a CIGS-based ink. By way of example, and without limitation, $Cu(Ac)_2$ (445 mg) and/or $In(Ac)_3$ (720 mg) and 240 mg of selenourea may be dissolved in 70 mL of doubly distilled water and sonicated for about 1 hour under an atmosphere of argon, at room temperature. A round-bottom Pyrex glass vessel (total volume 70 mL) may be used for the ultrasound irradiation. The temperature of the mixture rises gradually to about 80° C. during ultrasonic irradiation. After about 1 hour of sonication, the solution may be centrifuged, and the precipitate washed with water and then with absolute ethanol.

3. Elemental Metal Nanoparticles of Cu, In and Cu—In Alloy with Se(S) Vapor or Powders In a preferred embodiment, the nanoparticles for the ink may be prepared from a mixture of metal nanoparticles and a vapor or powder containing either Se or S. Metal nanoparticles have been prepared by a wide variety of techniques including but not limited to laser ablation, nucleation from vapor, exploding wires by electrical current surge, thermal decomposition of organometallic compounds, sonolysis, pulse radiolysis, electrochemical reduction and chemical reduction of the corresponding metal salts, and the like. Reduction of metal salts in the presence of a suitable protecting agent is a commonly used technique. Generally, a reductant, such as borohydride, hydrotriorganoborates, hydrogen or citrate, is added to a solution of the corresponding metal salt. An easily oxidized solvent may function both as the electron donor and the dispersing medium. Such particles are of particular interest for catalysis, as the metal surface is readily accessible. Alcohols and ethers have been quite extensively used for this purpose. Metal nanoparticles have a tendency to agglomerate, and therefore, it is necessary to protect them using surfactants or polymers, such as cyclodextrin, PVP, PVA, citrate or quaternary ammonium salts. In another strategy, the metal salt is reduced in micelles. A wide variety of ultra-fine colloidal surfactant-micelle protected metal nanoparticles can be successfully synthesized in solution. The size distribution of the metal nanoparticles may be controlled, e.g., by size-selective precipitation, ultrafiltration and the like.

Such metal colloids can be prepared in an ink formulation. After being mixed with Se (or S) fine powders, the ink can be coated on substrate and then subject to heat treatment to drive a reaction of the type:

$$(IB\ nanoparticle) + (IIIA\ nanoparticle) + VIA + HEAT \rightarrow IB\text{-}IIIA\text{-}VIA$$

By way of example, IB may be Cu, IIIA may be In and/or Ga, and VIA may be Se or S.

The reaction between metal or metal alloy nanoparticles and Se (or S) powder forms CIGS (or CIS) film. The ink may include a homogeneous mixture of metallic particles and powders of group VIA materials. The individual metallic particles are generally uniformly distributed throughout a matrix of, e.g., Se or S powder. Sub-micron-sized metallic particles may be formed by methods involving mechanical comminution, e.g., milling, grinding, crushing and the desired size distribution obtained, e.g., by ultrafiltration or size-selective precipitation.

In addition, nanometer-scale particles may be prepared by a gas condensation method. For example, in the gas condensation method, a metal may be heated to a vapor. The vapor then collects and condenses into particles. Such a technique may produce particles that are nominally spherical, approximately 30-40 nm in diameter and having a very tight size distribution (e.g., ±5 nm to ±10 nm). See also "Ultrafine Metal Particles", C. G. Granqvist and R. A. Buhrman, J., Appl. Phys., 47, 2200, (1976).

In another embodiment, the metal particles may be prepared by exploding fine metal wires with a surge of electrical current. For example, metal wires 7.5-25 microns in diameter may be exploded in a liquid such as water or alcohol by applying an increasing DC voltage across the wire until it explodes, e.g., at a few tens of volts. The resulting particles remain suspended in the liquid. Copper wires exploded in this fashion can produce particles about 30 to 70 nm in diameter.

The metal nanoparticles and group VIA powder may be mixed together with an optional binder to form a green microstructure. The binder serves to hold the metallic particles together, provides lubrication while the particles are mixed, and then or vaporizes completely during the sintering process leaving no trace of the binder in the final metallic product. Preferably, the binder combusts or vaporizes completely during the sintering process leaving no trace of the binder in the final CI(G)S active layer. Binders useful in conjunction with such embodiments of the invention include, but are not limited to, wax- or oil-based binders such as Acrawax® C® (Glyco), Advawax® 240, 275, 280, 290 (Carstab), Eramid® (Hexcel), Glucolube® VL (Glyco), Hostalub® FA 1 (Amer. Hoechst), HSTA 1, 3 (Hexcel), Interstab® G-8257, Kantstik® S powder (Specialty Prod.), Kemamide® W-20, W-40, E (Humko Chem.), Nopcowax® 22DS (Synthetic Prod.), Paricin® 285, 220 (NL Industries), Ross Wax® 140 (Frank B. Ross), and Slip-Eze®, Slip-Quick®, Vyn-Eze® (Hexcel) and the like; lower alkanols ($C_1$-$C_6$ alkanols, preferably $C_1$-$C_4$ alkanols) such as ethanol, isopropanol, and the like; or traditional dispersant/binder systems used in ceramic possessing, such as polymethacrylate/polyvinyl alcohol/polyethylene glycol systems.

In some embodiments, the metal particles may be formed into a paste mixture comprising the elemental metal particles along with a resin, solvent, wetting agent, and flow control agent. In addition, pastes can be made by combining elemental metals or other metallic particles with a polymer. Furthermore, a nanopowder of metal particles may be added to polymer matrix materials. Examples of suitable polymer matrix materials include poly(methyl methacrylate) (PMMA), poly (vinyl alcohol) (PVA), polycarbonates, polyalkenes, and polyaryls. In addition dispersants, binders, detergents, modifiers, or additives may be included along with the matrix material. Examples of modifiers or additives include plastisols, thickeners, or thinners to change the viscosity or change or improve the smoothness of the ink film surface. For example, "Viscosity Buster 10025VB" from Wilflex, at about a 1% concentration typically stabilizes and can improve the flow properties of ink. Additional modifiers or additives include, e.g., acids or bases to change pH of the ink or additives that lower the flash temperature of the ink and retarders or reducers to change the drying time of the ink. Potential sources of such modifiers and additives include Wilflex, Rutland Inks of Pineville, N.C., Chemical Consultants, Inc. of Corona, Calif., Union Inks of Singapore.

In the event that the nanoparticles are subject to oxide formation on the surface of the particles, for example, copper particles having a coating of copper oxide, the molding composition may additionally comprise a fluxing agent. The fluxing agent serves to substantially halt formation of the oxide layer, thereby enhancing the ability of the molding composition to form the green microstructure and aiding in the final sintering process. Examples of common fluxing agents in general use include abietic acid, stearic acid, hydrochloric acid, amine hydrochlorides and amine resins. Either a suitable commercial flux formulation or a specially formulated fluxing agent may be utilized. Further, to minimize or eliminate oxide formation on the surface of the nanoparticles, the nanoparticles can be formed in an atmosphere that lacks oxygen, e.g. a nitrogen-filled glovebox.

4. Liquid Metal Based Inks

In another embodiment, the liquid ink may be made using one or more liquid metals. For example, an ink may be made starting with a molten mixture of Gallium and/or Indium (commercially available, e.g., from Alfa Aesar of Ward Hill, Mass.). Copper nanoparticles may then be added to the mixture, which may then be used as the ink/paste. Copper nanoparticles are available commercially, e.g., from Materials Modification Inc., of Fairfax, Va. Alternatively, the temperature of the Cu—Ga—In mixture may be adjusted (e.g. cooled) until a solid forms. The solid may be ground at that temperature until small nanoparticles (e.g., less than 5 nm) are present. Selenium may be added to the ink and/or a film formed from the ink by exposure to selenium vapor, e.g., before, during, or after annealing.

5. Organometallic Liquid Inks

In yet another embodiment, the liquid ink may be made using one or more organometallic precursors of IB, IIIA and VIA elements. For instance, examples of copper precursors include Copper II hexafluoropentanedionate (Gelest SKU#AKC253); Copper II methoxide (Gelest SKU#AKC254); Copper II ethoxide (Gelest SKU#AKC250); and Copper II ethylacetoacetate (Gelest SKU#AKC252), all of which are available from Gelest, Inc. of Morrisville, Pa. Examples of indium precursors include Indium 2,4-Pentanedionate (Gelest SKU#AKI370), also called indium acetylacetonate; Indium Methoxyethoxide (Gelest SKU#AKI365); and Indium methyl(trimethyl)acetylacetate (Gelest SKU#AKI373), also all available from Gelest. Examples of Gallium precursors: Gallium III 2,4-Pentanedionate (Gelest SKU#AKG310); and Gallium III Ethoxide (Gelest SKU#AKG320), also available from Gelest.

The precursors may be mixed as liquids to form the ink. The organic components may be burned out of the ink by heating at about 500° C., e.g., after a film of the ink is disposed on a substrate. Alternatively, a sol-gel may be formed from organometallics of e.g., Cu, In, and/or Ga. In general, the sol-gel processing involves the transition of a system from a liquid "sol" (mostly colloidal) into a solid "gel" phase. The starting materials used in the preparation of the "sol" are usually inorganic metal salts or metal organic compounds such as metal alkoxides along with water, alcohol and, optionally, a small amount of acid.

For example, the ink may be fabricated by making a pseudo sol out of mixed metal organic precursors, such as alkoxides or diketonates of Copper, indium, gallium in the desired stoichiometric ratio. By way of example, copper(II)ethoxide or Copper(II)ethylacetoacetate may be mixed with gallium(III) ethoxide or gallium(III)pentanedionate and with indium(III) methoxyethoxide or indium(III) 2,4 pentanedionate. A sol may be formed by adding water, an alcohol and, optionally, an acid, to the mixed metal organic precursors. The sol may be coated in a dish (e.g. drop cast), annealed to remove labile groups, and allow drying to form a powder. Note that this process can be scaled to bulk in high volume. The metallic powder can then be milled and mixed with dispersant and then coated, and the resultant film can then be reduced by treatment with $H_2$ and/or $N_2$ at 400° C., after which 10-50 mbar Se vapor can be introduced to selenize the film. Alternatively, the powder compounds can be first reduced to metals through exposure to $H_2$ gas, then mechanically milled and/or ground up mixed with dispersant and then coated.

6. Metal Halides Dissolved in Chelating Agents

In yet another embodiment, a metal halide (MCl or MI, where M is a metal) could be dissolved in any of a number of chelating agents, then (optionally) mixed in water to keep the metals in solution. The solution mixture can then serve as a basis for a precursor paste or ink. Suitable metal halides include chlorides and iodides of the group IB, IIIA and VIA metals. Suitable chelating agents include, but are not limited to, e.g. amines, diamines such as ethylene diamine, polyamines, polyethylene glycol, low molecular weight alcohols, ketones, diketones, carboxylic acids, and mixtures thereof.

7. Metal Salts

Metal salts and other metal compounds can also be used as reagents to synthesize metal nanoparticles. Provided that they exhibit proper reactivity, suitable metal salts and other metal compounds include but are not limited to metal halogenides, metal nitrates, metal nitrites, metal nitrides, metal sulfates, metal sulfites, metal sulfides, metal alcoholates, metal phosphates, metal phenolates, metal carbonates, metal carboxylates, and blends or mixtures of these salts. For example, for each element or non-oxide compound from the group IB, IIIA and VIA metals, metal salts can be synthesized or purchased (e.g., through Sigma-Aldrich of St. Louis, Mo.), formed or purified as nanoparticulates, then each of the nanoparticulates can be intermixed in the proper ration to serve as the basis for an ink for effective CIGS absorber layer function.

Photovoltaic Devices

The nanoparticles are generally mixed with an organic or inorganic solvent to form the ink. In some embodiments of the invention, the nanoparticles may be mixed with water to form an aqueous suspension that serves as the basis of the ink. Schulz, by contrast teaches non-aqueous colloidal suspensions and stresses that every effort should be made to avoid introducing even incidental amounts of water into his colloidal suspensions in order to avoid agglomeration of particles. In fact, aqueous suspensions have several advantages over non-aqueous suspensions during ink formation and deposition. First, water is an inexpensive solvent, and it is much easier to scale to high-volume production processes. In contrast, organic solvents are inherently more expensive and hazardous than water, and waste solvents and other organic byproducts incur costs resulting from waste processing. Second, a wide variety of water-compatible dispersants can easily be added to an aqueous suspension of nanoparticles, which are stabilized by the dispersant, which keeps the nanoparticles separated from each other until the annealing step melts them together. In contrast, if such water-compatible dispersants were added to an organic (non-aqueous) solution, such a mixture may form two phases as a result of organic-inorganic partitioning in the solution. In this case, nanoparticles that were initially stabilized by capping agents may subsequently collapse and form aggregates, leading to non-uniform coatings. Examples of suitable dispersants include Tamol™ and Duramax™ from Rohm and Haas of Philadelphia, Pa. Further information on Tamol™ may be found at http://www.rohmhaas.com/coatings/dispersants.html. Further information about Duramax™ may be found at http://www.rhcis.com/markets_and_products/electronic.html.

Note that, as used herein, the term "aqueous suspension" refers to the ink at the end of its manufacture. The use of the term "aqueous" does not exclude the possibility that during manufacture, the particles may be dispersed in an organic solvent or some solvent other than water. For example, if the particles are capped with organic ligands and in some of the particle formation chemistries, the particles may be initially made in alcohol or another organic solvent then later precipitated or isolated for resuspension in water to form the ink. Furthermore, in some embodiments of the present invention, the particles may be so small that they form liquids, e.g., the particles may be as small as individual atoms or molecules.

The liquid ink (aqueous or otherwise) may be spread in a thin film over a substrate using solution based coating techniques such as web coating, spray coating, spin coating, doctor blade coating, printing techniques including contact printing, gravure printing, microgravure printing, ink-jet printing, jet deposition, and the like. Such a film can be deposited on a flexible substrate, in a roll-to-roll manner using a commercially available web coating system. The film may then be heated to remove the solvent and to sinter the nanoparticles together to form a layer of a IB-IIIA-VIA alloy. The alloy may have the general formula $CuIn_{1-x}Ga_x(S, Se)_2$, where x is between 0 and 1. The reduced temperature sintering (e.g., from about 200° C. to about 600° C.) made possible by the small particle size and narrow size distribution facilitates forming CIGS films in a high volume roll-to-roll production environment on thin flexible substrates such as metal foils or metallized plastic films. To heat and sinter the film, if deposited on a flexible substrate, the film can be wound into a coil and the coil can be heated such that the entire roll is heated at the same time, substantially increasing the scaleability of the heating process through such a high-volume batch process. Examples of processing a coiled substrate are described e.g., in U.S. patent application Ser. No. 10/782,545 titled "HIGH THROUGHPUT SURFACE TREATMENT ON COILED FLEXIBLE SUBSTRATES", which has been incorporated by reference.

Some high-volume batch processes for coating the substrate with the ink, e.g., chemical bath deposition (CBD) for liquid-based deposition, and atomic layer deposition (ALD) for gas- and vapor-based deposition, could potentially coat both sides of a coiled substrate at one time. However, it may be desirable to primarily coat only one side, since double-sided coating can result in waste of valuable components of the ink, e.g., indium. To avoid such waste, two substrates may be attached together "back-to-back" to form a dual substrate having, in effect, two front sides. The dual substrate may then be wound into a coil and coated such that both front surfaces get coated while the back surfaces do not. Preferably, the substrates are attached in a manner that allows them to be separated from each other after processing. By way of example the substrates may be attached with a low-strength adhesive or electrostatic film applied to the back side of one or both substrates. Alternatively, an edge where the two substrates join may be sealed, e.g., with a tape, so that reactants cannot reach the back sides during processing. Processing the substrate in this fashion wastes less of the ink and may increase the area of the substrate that can be coated at one time.

Figure 2:
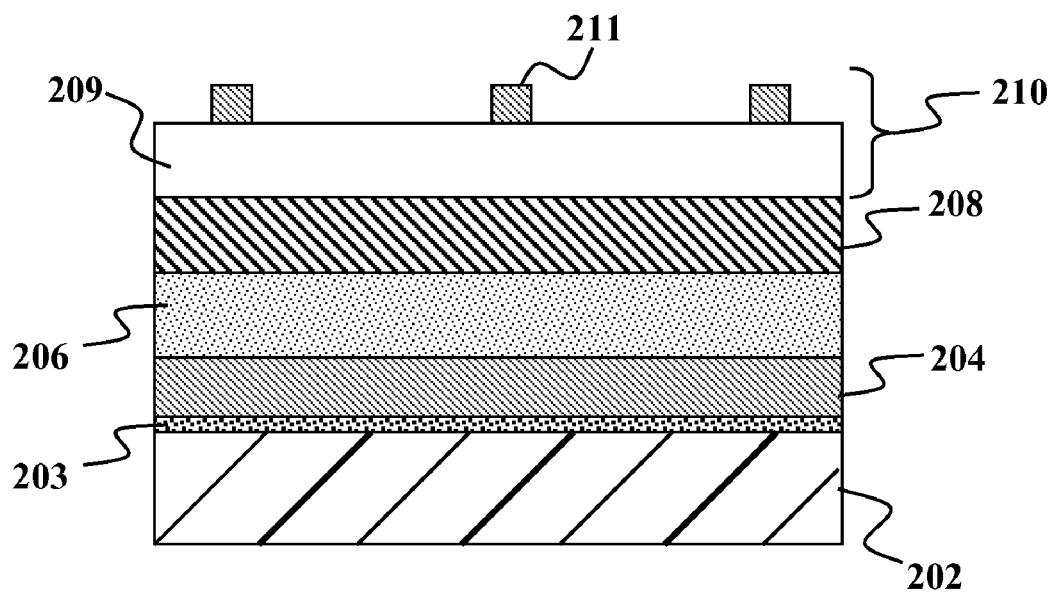
FIG. 2 is a schematic diagram of a photovoltaic cell according to an embodiment of the present invention.

The IB-IIIA-VIA alloy layer can be used in the active layer of photovoltaic cell, e.g., of the type shown in FIG. 2. The solar cell 200 generally includes a substrate or base layer 202, a base electrode 204, a IB-IIIA-VIA layer 206, a window layer 208, and a transparent electrode 210. The base layer 202 may be made from a thin flexible material suitable for roll-to-roll processing. By way of example, the base layer may be made of a metal foil, such as titanium, a polymer such as polyimide or a metallized plastic. The base electrode 204 is made of an electrically conducive material. By way of example, the base electrode 204 may be a layer of stainless steel or molybdenum, e.g., about 0.5 micron to about 1 micron thick.

By way of example, and without limitation, the IB-IIIA-VIA layer 206 may include material of the general formula $CuIn_{1-x}Ga_x(S$ or $Se)_2$. The IB-IIIA-VIA layer 206 may be fabricated by depositing a film of a nanoparticle-based ink, paste or slurry, e.g., roughly 4 to 5 microns thick when wet on the base electrode 204. The film may be annealed by heating to a temperature sufficient to burn off any binders or cap layers on the particles and sinter the particles together. The IB-IIIA-VIA 206 layer may be about 1 micron to about 2 microns thick after annealing. By using nanoparticles of the average size and size distribution described above, the ink, paste or slurry may be annealed at a temperature compatible with the underlying substrate 202 and electrode 204. An optional adhesion layer 203 may facilitate bonding of the electrode 204 to the substrate 202.

After annealing, the film may optionally be exposed to selenium vapor at about 300-500° C. for about 30-45 minutes to ensure the proper stochiometry of Se in the film. To carry out such a Se vapor exposure, the film, if deposited on a flexible substrate, can be wound into a coil and the coil can be coated so that the entire roll is exposed at the same time, substantially increasing the scaleability of the Se vapor exposure process through such a high-volume batch process, e.g., as described above.

The window layer 208 is typically used to smooth out the "slope" between the bandgaps of the different materials making up the IB-IIIA-VIA layer 206. By way of example, the bandgap adjustment layer may include cadmium sulfide (CdS), zinc sulfide (ZnS), or zinc selenide (ZnSe) or some combination of two or more of these. Layers of these materials may be deposited, e.g., by chemical bath deposition, to a thickness of about 50 nm to about 100 nm.

The transparent electrode 210 may include a transparent conductive oxide layer 209, e.g., zinc oxide (ZnO) or aluminum doped zinc oxide (ZnO:Al), which can be deposited using any of a variety of means including but not limited to sputtering, evaporation, CBD, electroplating, CVD, PVD, ALD, and the like. If the substrate is flexible and the deposition technique is ALD or CBD or the like, a coiled/wound flexible substrate can be exposed so that the entire roll is processed at one time, e.g., as described above. The transparent electrode 210 may further include a layer of metal (e.g., Ni, Al or Ag) fingers 211 to reduce the overall sheet resistance.

An optional encapsulant layer (not shown) provides environmental resistance, e.g., protection against exposure to water or air. The encapsulant may also absorb UV-light to protect the underlying layers. Examples of suitable encapsulant materials include one or more layers of polymers, such as polyethylene terephthalate (PET), ethylene vinyl acetate (EVA), and/or Mylar®. Mylar is a registered trademark of E. I. du Pont de Nemours and Company of Wilmington, Del. Inorganic materials, such as glass and plastic foils, metalized plastic foils, and metal foils may also be used for the encapsulant layer. The encapsulant layer may also include nitrides, oxides, oxynitrides or other inorganic materials. Alternatively, the encapsulants may include Tefzel® (DuPont), tefdel, thermoplastics, polyimides, polyamides, nanolaminate composites of plastics and glasses (e.g. barrier films), and combinations of the above. For example, a thin layer of (expensive) EVA/polyimide laminated to thick layer of (much less expensive) PET.

Embodiments of the present invention provide for low-cost, high-volume production of large area photovoltaic devices without having to undergo selenization with hazardous $H_2Se$ or reduction of oxides in $H_2$. Furthermore, embodiments of the present invention are compatible with roll-to-roll manufacturing of photovoltaic cells and modules that can be readily scaled up to high production volumes.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. The appended claims are not to be interpreted as including means-plus-function limitations, unless such a limitation is explicitly recited in a given claim using the phrase "means for."

What is claimed is:

1. A method for fabricating liquid ink comprising:
   forming non-oxide metal nanoparticles containing elements from group IB;
   forming non-oxide metal nanoparticles from group IIIA; and
   adding one or more liquid metals containing one or more elements of group IIIA;
   intermixing the non-oxide nanoparticles from groups IB and IIIA and one or more liquid metals from group IIIA, wherein the particles are in a desired particle size range of between about 0.1 nm and about 500 nm in diameter, wherein, for each element metal, a majority of the mass of the metal nanoparticles range in size from no more than about 40% above or below an average particle size, or, if the average particle size is less than about 5 nanometers, from no more than about 2 nanometers above or below the average particle size; and
   mixing the particles to form a liquid that serves as an ink.

2. The method of claim 1 wherein forming the non-oxide metal nanoparticles comprises using one or more methods selected from the group consisting of: laser ablation, mechanical milling, grinding, nucleation from vapor, exploding wires by electrical current surge, thermal decomposition of organometallic compounds, sonolysis, pulse radiolysis, electrochemical reduction, and chemical reduction.

3. The method of claim 1 further comprising adding group VIA material to the liquid ink.

4. The method of claim 1, wherein a Group VIA element is introduced into the liquid ink by adding particles containing one or more Group VIA element.

5. The method of claim 1, wherein a Group VIA element is introduced by heating the ink in a Group VIA vapor.

6. The method of claim 1, wherein the particles containing the containing one or more elements of group IB are alloy particles.

7. The method of claim 1 further comprising mixing the particles with an organic solvent to form the liquid ink.

8. The method of claim 1 further comprising mixing the particles with an inorganic solvent to form the liquid ink.

9. The method of claim 1 wherein the particles are mixed with water to form the liquid ink.

10. The method of claim 1 further comprising adding a dispersant to the liquid ink.

11. The method of claim 1, further comprising adding one or more surfactants, polymers, dispersants, binders, modifiers, detergents or additives to the liquid ink.

12. The method of claim 1 further comprising adding a binder to the nanoparticles.

13. The method of claim 1 further comprising adding a fluxing agent to the nanoparticles.

14. The method of claim 13 wherein forming a suspension of non-oxide quantum nanoparticles includes sonochemical synthesis of nanoparticles particles containing Se with Cu or In or Ga.

15. The method of claim 1 further comprising adding a water-compatible dispersant to the liquid.

16. The method of claim 1 wherein forming the non-oxide nanoparticles includes preparing particles in a non-oxygen atmosphere.

17. The method of claim 1 wherein forming comprises combining the non-oxide nanoparticles in a solvent to form a suspension.

18. The method of claim 1 wherein forming comprises combining the non-oxide nanoparticles in a solvent to form a colloidal suspension.

* * * * *